（12）United States Patent
Lachenbruch et al.

(10) Patent No.: US 8,800,078 B2
(45) Date of Patent: Aug. 12, 2014

(54) LOCALIZED MICROCLIMATE MANAGEMENT

(71) Applicant: Hill-Rom Service, Inc., Batesville, IN (US)

(72) Inventors: Charles A. Lachenbruch, Lakeway, TX (US); Timothy J. Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 14/049,273

(22) Filed: Oct. 9, 2013

(65) Prior Publication Data

US 2014/0041118 A1    Feb. 13, 2014

Related U.S. Application Data

(63) Continuation of application No. 13/688,670, filed on Nov. 29, 2012, now Pat. No. 8,578,527, which is a continuation of application No. 12/493,456, filed on Jun. 29, 2009, now Pat. No. 8,327,477.

(51) Int. Cl.
    *A47C 21/04* (2006.01)
(52) U.S. Cl.
    USPC ............ 5/421; 5/423; 607/96; 607/104
(58) Field of Classification Search
    USPC ........ 5/421, 423, 690; 607/98, 104, 108, 112, 607/114, 96
    See application file for complete search history.

(56) References Cited

U.S. PATENT DOCUMENTS

| 3,738,702 | A | 6/1973 | Jacobs |
| 3,888,259 | A | 6/1975 | Miley |
| 5,800,480 | A | 9/1998 | Augustine et al. |
| 6,033,432 | A | 3/2000 | Augustine |
| 6,772,825 | B2 * | 8/2004 | Lachenbruch et al. ......... 165/46 |
| 7,273,490 | B2 | 9/2007 | Lachenbruch |
| 7,727,267 | B2 * | 6/2010 | Lachenbruch ............... 607/108 |
| 8,327,477 | B2 | 12/2012 | Lachenbruch et al. |
| 8,578,527 | B2 | 11/2013 | Lachenbruch et al. |
| 2005/0288749 | A1 | 12/2005 | Lachenbruch |
| 2006/0085919 | A1 | 4/2006 | Kramer et al. |
| 2006/0162074 | A1 * | 7/2006 | Bader ............................... 5/421 |
| 2007/0135878 | A1 | 6/2007 | Lachenbruch et al. |
| 2007/0272673 | A1 * | 11/2007 | Keane ........................... 219/212 |
| 2010/0325796 | A1 | 12/2010 | Lachenbruch et al. |

FOREIGN PATENT DOCUMENTS

| EP | 0862901 | 9/1998 |
| EP | 1779824 | 5/2007 |
| WO | WO 2006/023479 | 3/2006 |
| WO | WO 2007/016054 | 2/2007 |

OTHER PUBLICATIONS

European Search Report, "Application No. EP 10251104", (Sep. 27, 2010), The Hague.

(Continued)

*Primary Examiner* — Fredrick Conley
(74) *Attorney, Agent, or Firm* — Barnes & Thornburg LLP (57) ABSTRACT

An occupant support includes a mattress 20, a detector 54 and an energy management system comprising thermally conductive pathways and a controller 60. The controller activates one or more selected pathways in response to information from the detector to regulate energy transfer at a detected region of risk 66 on the mattress.

20 Claims, 11 Drawing Sheets

(56) References Cited

OTHER PUBLICATIONS

Paul A. Iaizzo, PhD, Temperature Modulation of Pressure Ulcer Formation: Using a Swine Model, From the Departments of Surgery and Physiology, University of Minnesota, Minneapolis, Minnesota, Wounds 2004; 16 (11): 336-343.

Paul A. Iaizzo, PhD, Craig L. Kveen, BS, Jaydeep Y. Kokate, MS, Keith J. Leland BS, Gary L. Hansen, MS, Ephraim M. Sparrow, PhD, Prevention of Pressure Ulcers by Focal Cooling: Histological Assessment in a Porcine Model, Wounds 1995; 7 (5): 161-169, Sep./Oct. 1995.

* cited by examiner

LOCALIZED MICROCLIMATE MANAGEMENT

CROSS-REFERENCE TO RELATED APPLICATIONS

The present application is a continuation of U.S. application Ser. No. 13/688,670, filed Nov. 29, 2012, now U.S. Pat. No. 8,578,527, which is a continuation of U.S. application Ser. No. 12/493,456, filed Jun. 29, 2009, now U.S. Pat. No. 8,327,477, and each of which is hereby incorporated by reference herein.

TECHNICAL FIELD

The subject matter described herein relates to microclimate management of a bed or other occupant support, and particularly to localized control of a microclimate system comprising high thermal conductivity pathways.

BACKGROUND

Hospital beds and other occupant supports include a frame and a mattress or other occupant interface. An occupant confined to the bed for an extended time may develop pressure ulcers, especially at the locations on the occupant's body that exert the most pressure on the occupant interface. The risk of an occupant developing pressure ulcers can be reduced by controlling the microclimate, i.e. parameters such as temperature in the immediate vicinity of the occupant. In particular, the risk of pressure ulcers can be reduced by cooling the susceptible portions of the occupant's body.

One way to control the microclimate involves the use of a "topper", an envelope of material that rests on the mattress so that the topper, rather than the mattress itself, serves as the occupant interface. The topper has a fluid inlet and a fluid outlet. In operation, a blower forces a fluid, usually ambient air, into the interior of the topper by way of the inlet. The air enters the topper and discharges to the environment through the outlet. The flow of ambient air through the topper helps convect heat away from the parts of the occupant's body in contact with the topper, and thereby reduces the risk of pressure ulcers. Heat convection can be enhanced by using chilled air rather than ambient air.

Although microclimate management toppers as described above are effective they are not without limitations. The heat withdrawal capacity of the described topper is substantially spatially uniform, i.e. it's potential for extracting heat from those portions of the occupant's body that bear heavily on the occupant interface is the same as its potential for extracting heat from those portions of the occupant's body that bear lightly on the interface (and which therefore don't require as much heat extraction). The uniformity of heat extraction potential even extends to those portions of the topper not in contact with the occupant. In addition, the fact that a large portion of the occupant's body contacts the topper means that the benefits of using chilled air can be offset by the associated risk of hypothermia. Although the risk of hypothermia might be addressed by compartmentalizing the topper and directing air only to selected compartments or zones, such an approach complicates the architecture of the topper and requires ductwork and valves that increase the weight, cost and complexity of the bed and adversely affect bed transportability, marketability and reliability.

What is needed is an occupant support having localizable microclimate management capabilities while avoiding at least some of the disadvantages described above.

SUMMARY

An occupant support includes a mattress, a detector and an energy management system comprising thermally conductive pathways and a controller. The controller activates one or more selected pathways in response to information from the detector to regulate energy transfer at a detected region of risk on the mattress.

The foregoing and other features of the various embodiments of the occupant support described herein will become more apparent from the following detailed description and the accompanying drawings.

DETAILED DESCRIPTION

FIGS. 1-4 show an occupant support comprising a mattress 20 having fluid filled bladders 22 enclosed in a bladder covering 24. The mattress has a head end border 26, a foot end border 28 longitudinally spaced from the head end border, a left flank 32 and a right flank 34 laterally spaced from the left flank. The bladders typically contain air but could also contain water or other liquid.

Figure 1:
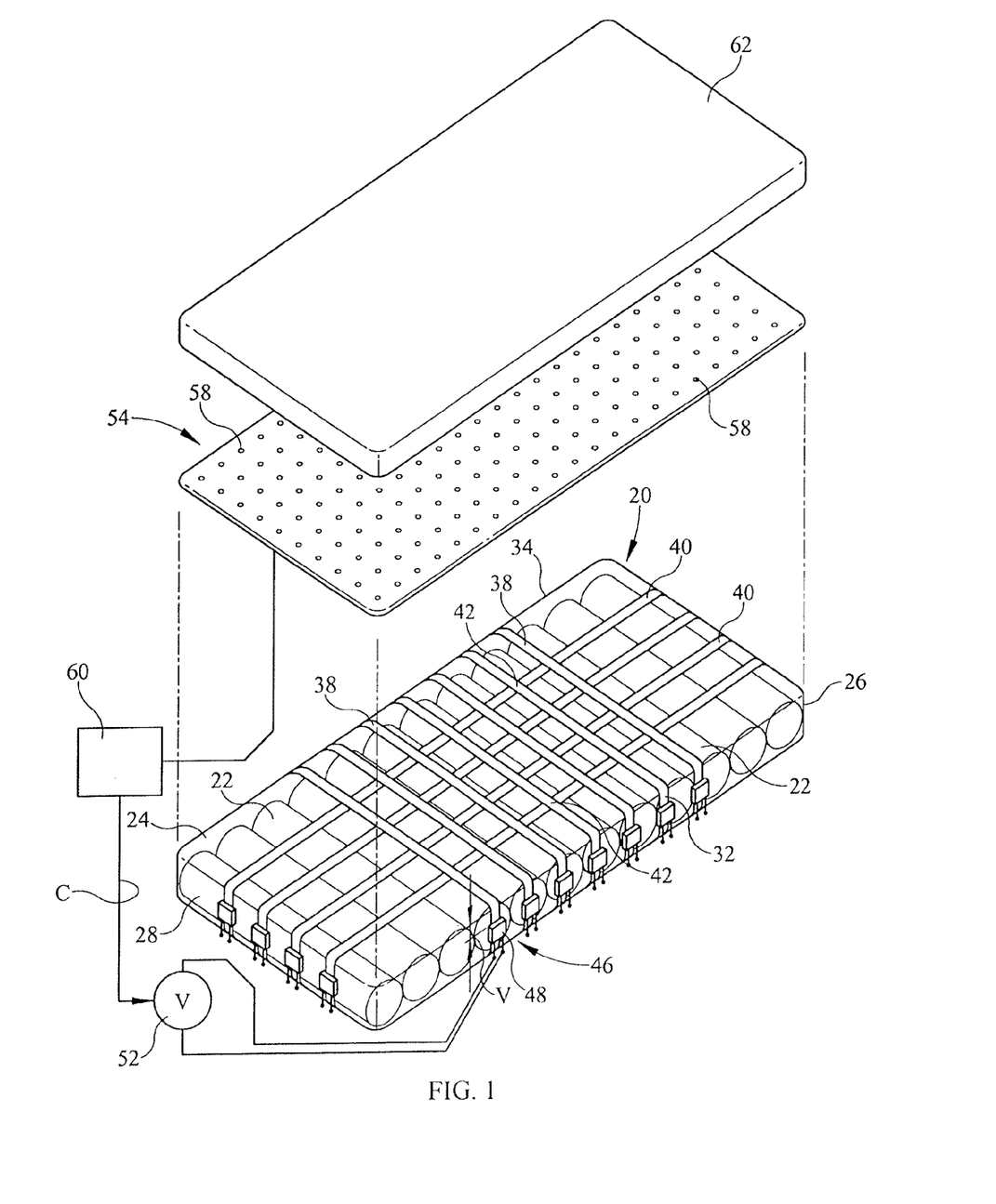
FIG. 1 is an exploded, schematic perspective view showing a mattress, a sensor array, a sensor cover, and a series of thermally conductive straps and associated heat flow augmentors.
Figure 2:
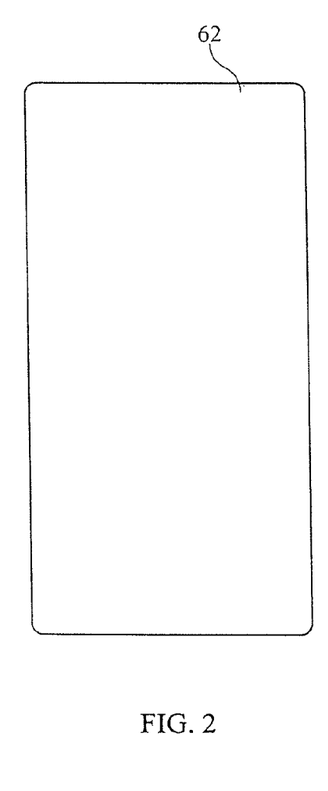
FIGS. 2-4 are plan views of the mattress, sensor array and sensor cover of FIG. 1.
Figure 3:
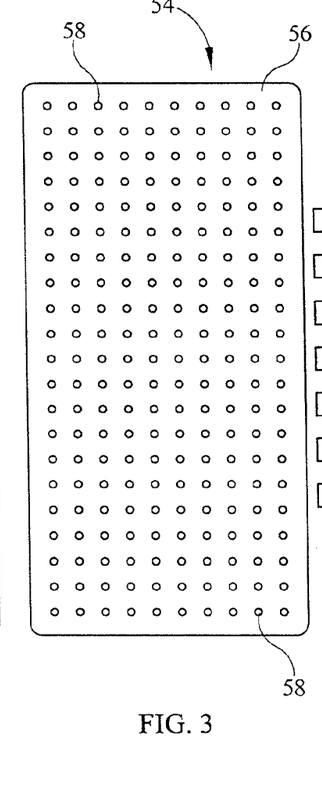
Figure 4:
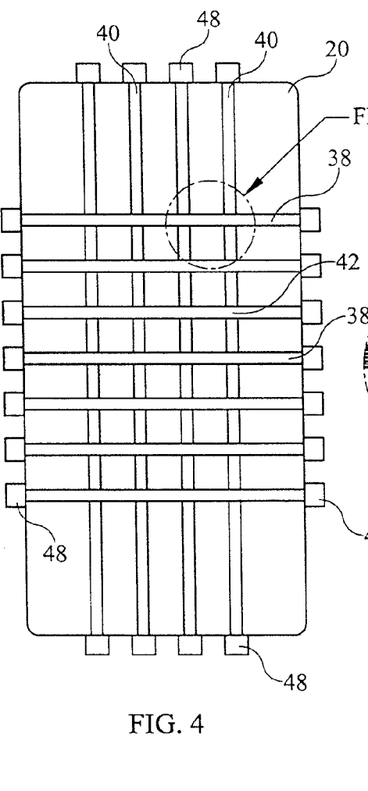

An energy management system includes a series of thermally conductive lateral straps 38 extending laterally across the covering and vertically along the left and right flanks 32, 34 and a series of thermally conductive longitudinal straps 40 extending longitudinally along the covering and vertically along the head and foot borders 26, 28. The lateral and longitudinal straps may contact each other at thermally conductive junctures 42 or may be thermally insulated from each other at the locations where they would otherwise intersect and form thermally conductive junctures. The term "juncture" and reference numeral 42 are used herein to refer to both an actual, thermally conductive juncture and a nonconductive juxtaposition of the lateral and longitudinal straps. The straps define thermally conductive pathways. Although FIG. 1 shows the use of both lateral and longitudinal straps it may not be necessary to employ both types.

Figure 5:
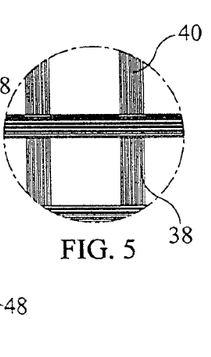
FIG. 5 is an enlarged view of a portion of FIG. 4 showing the thermally conductive straps.

As indicated most clearly in FIG. 5, the straps 38, 40 are made of a heat conducting material such as thermally conductive fibers having a thermal conductivity of at least about 4 Watts/meter/degree Kelvin. Examples of such fibers include pitch based carbon fibers and high conductivity polymers.

The energy management system also includes one or more heat flow augmentors 46 such as thermoelectric module 48. A thermoelectric module is a solid state device that converts electrical energy into a thermal gradient. Specifically, when a voltage source 52 applies a voltage to the leads of the thermoelectric module, one side of the thermoelectric module becomes cooler and is referred to as the cold side; the other side of the thermoelectric module becomes warmer and is referred to as the hot side. The cold side of a thermoelectric module contacts the left and right termini of each lateral strap and the head and foot termini of each longitudinal strap. The hot side of each thermoelectric module communicates with a heat sink, which in FIG. 1 is the ambient air. Although the foregoing discussion describes at least one thermoelectric module associated with each strap, it is also contemplated that an architecture in which only selected straps are outfitted with a thermoelectric module can be beneficial. To preserve the clarity of FIG. 1 only the connection between the voltage source and one of the thermoelectric modules is shown.

The occupant support also includes a detector 54 such as pressure sensor array 56 comprising multiple, individual pressure sensors 58 and a controller 60. A sensor cover 62 covers the sensor array. The quantity of pressure sensors may be equal to or may differ from the number of strap junctures. It is not necessary for the pressure sensors to be vertically juxtaposed over the strap junctures. As indicated schematically in FIG. 1 the controller communicates with the sensor array and issues a control command C.

Figure 6:
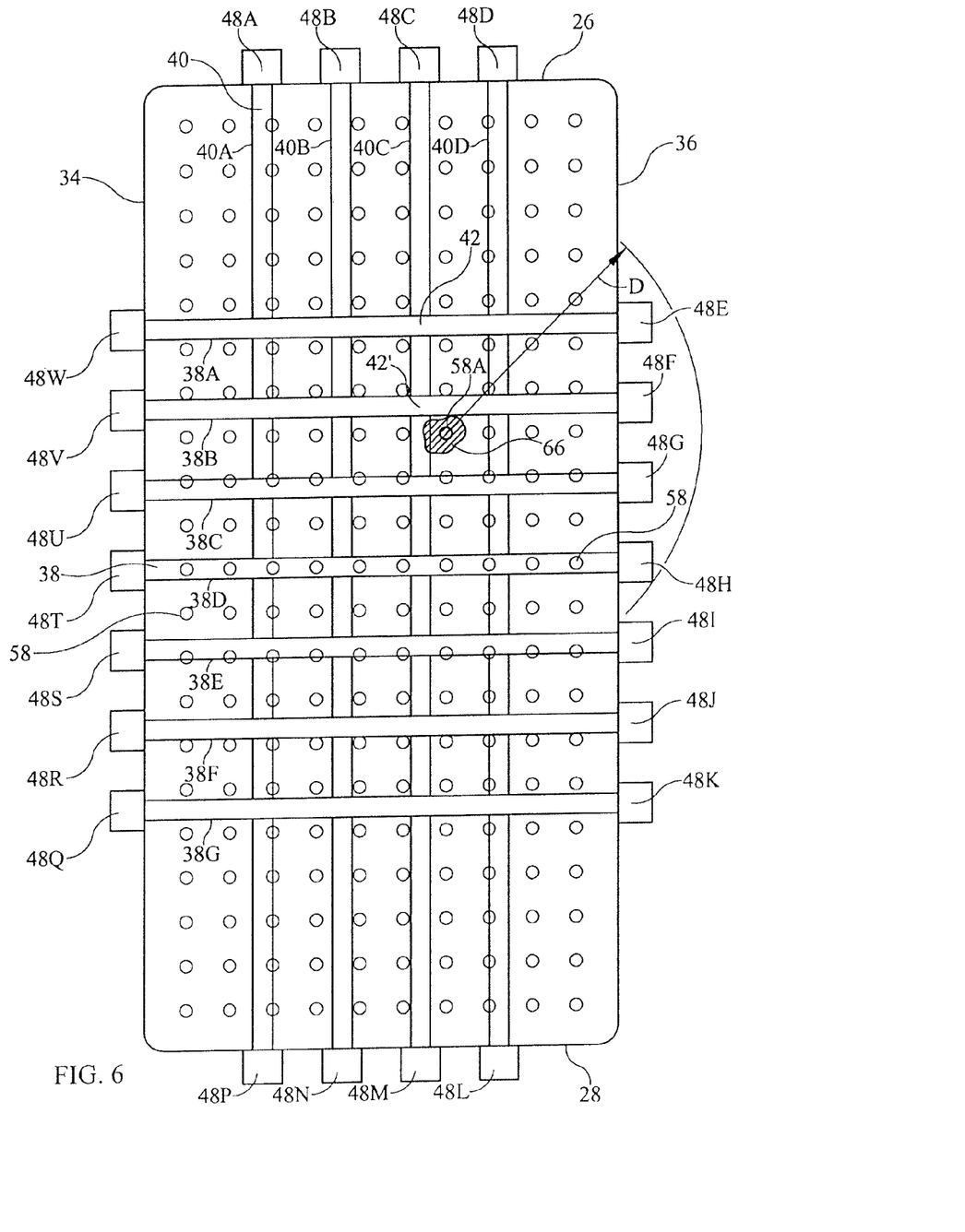
FIG. 6 is a plan view of the mattress showing the sensor array in relation to the thermally conductive straps and also showing a region of risk on the mattress.

When the mattress is occupied, the patient and the mattress exerts a spatially non-uniform pressure on each other. The locations where the pressure on the mattress is high correspond to the portions of the occupant's body susceptible to pressure ulcers and therefore define a region of risk on the mattress. The detector, e.g. the pressure sensor array, senses the pressure on the mattress. The controller receives information (e.g. pressure data) from the sensor array to determine the location of the region or regions of risk. The determination may rely on the magnitude of the pressure, the rate of change of pressure (dP/dt), the time during which pressure exceeds a threshold or combinations of these and/or other factors. For example pressure derivative could be used by adding air to a region at a known rate and monitoring the local pressure derivative. Heavily loaded regions will show a relatively rapid increase in pressure whereas more lightly loaded regions will show a relatively slower increase in local pressure. Once the location of the high risk region has been determined a control algorithm identifies certain thermoelectric modules as being effective for withdrawing a meaningful quantity of heat from a region or regions of risk and issues a command C to activate those modules. FIG. 6 shows a simple example in which the region of risk 66 corresponds to the location of a single pressure sensor 58A. One possible algorithm identifies the strap juncture 42' closest to the region of risk and activates thermoelectric module 48F, the thermoelectric module closest to the identified juncture, by commanding the voltage source to apply a voltage across the terminals of module 48F. Activation of module 48F augments the heat withdrawal through the portion of strap 38B between the juncture 48' and the module 48F. Another possible algorithm activates module 48F and its lateral partner module 48V. A third possible algorithm activates all four modules 48F, 48V, 48C, and 48M in contact with the straps 40C, 42B that define the juncture. A fourth possible algorithm activates all the thermoelectric modules within a specified horizontal distance D of the juncture, i.e. modules 48E, 48F, 48G and 48H. FIG. 6 shows distance D as a radius that encompasses all the thermoelectric modules that, when projected onto the plane of the radius, fall within the radius. In other words distance D doesn't account for the vertical distance V (FIG. 1) from the top of the mattress to the thermoelectric module. However the distance V could be accounted for if desired. A fifth possible algorithm activates a subset of modules whose operation will result in a desired amount of heat withdrawal. Note that "subset" can, in the limit, include all the modules. The desired amount of heat withdrawal may or may not be as much as the maximum heat withdrawal capacity of the energy management system. The amount of heat transfer augmentation attributable to each thermoelectric module can be controlled by regulating the voltage applied across its terminals.

Figure 7:
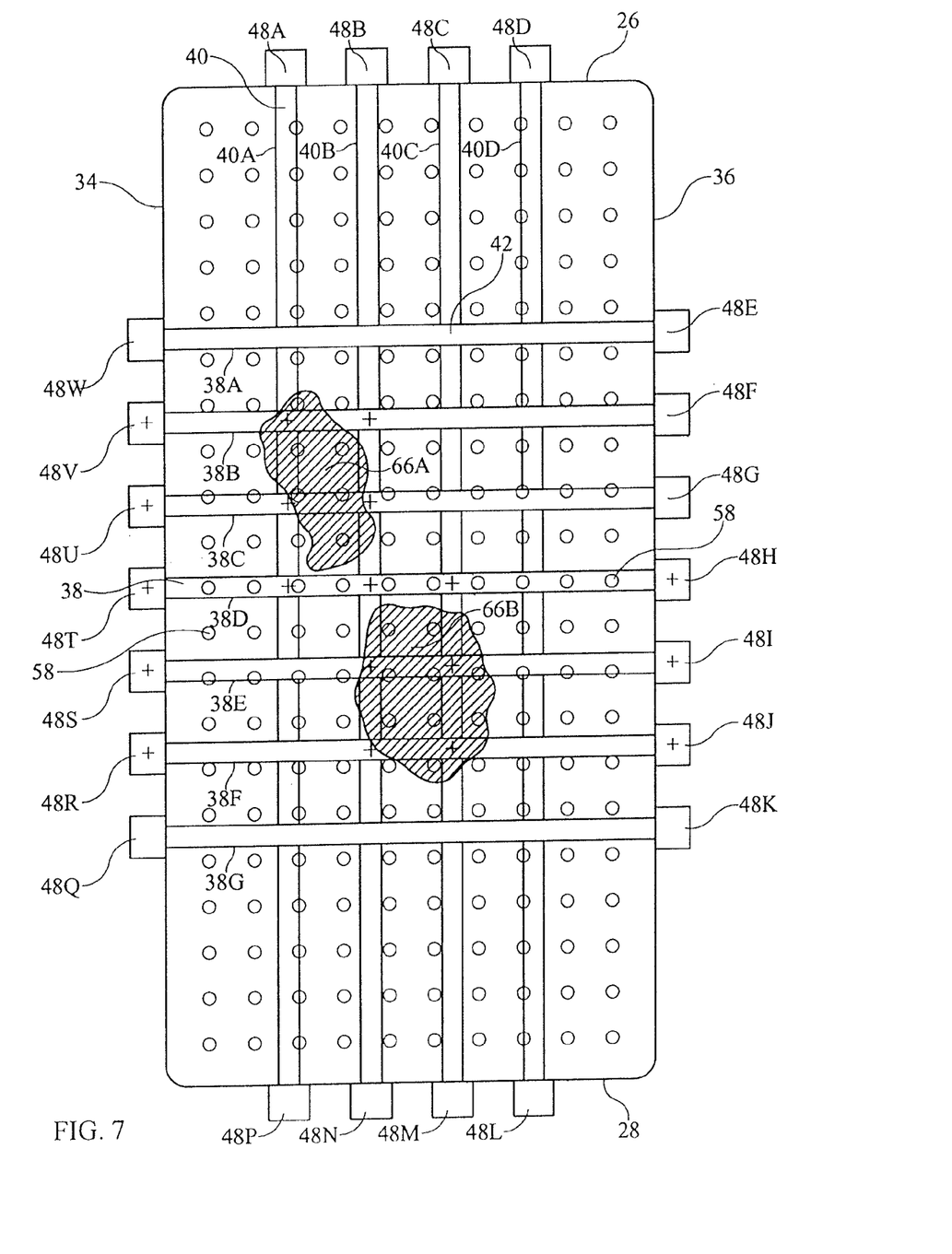
FIG. 7 is a view similar to that of FIG. 1 showing two regions of risk.

FIG. 7 shows multiple regions of risk 66A, 66B, each of which corresponds to multiple sensors. The fact that the borders of regions 66A and 66B (and region 66 in FIG. 6) do not coincide exactly with the locations of the individual pressure sensors 58 reflects the possibility that the algorithm for determining the boundary of a risk region could extrapolate beyond and/or interpolate between the exact locations of the sensors. The control algorithm has selected the strap junctures identified with a plus sign as the junctures corresponding to a region of risk, with the juncture at the juxtaposition of straps 40B and 38D corresponding to both regions 66A and 66B. The plus signs superimposed on thermoelectric modules 48H, 48I, 48J, 48R, 48S, 48T, 48U and 48V signify that the algorithm has activated those modules to transfer heat away from the two regions of risk.

Figure 8:
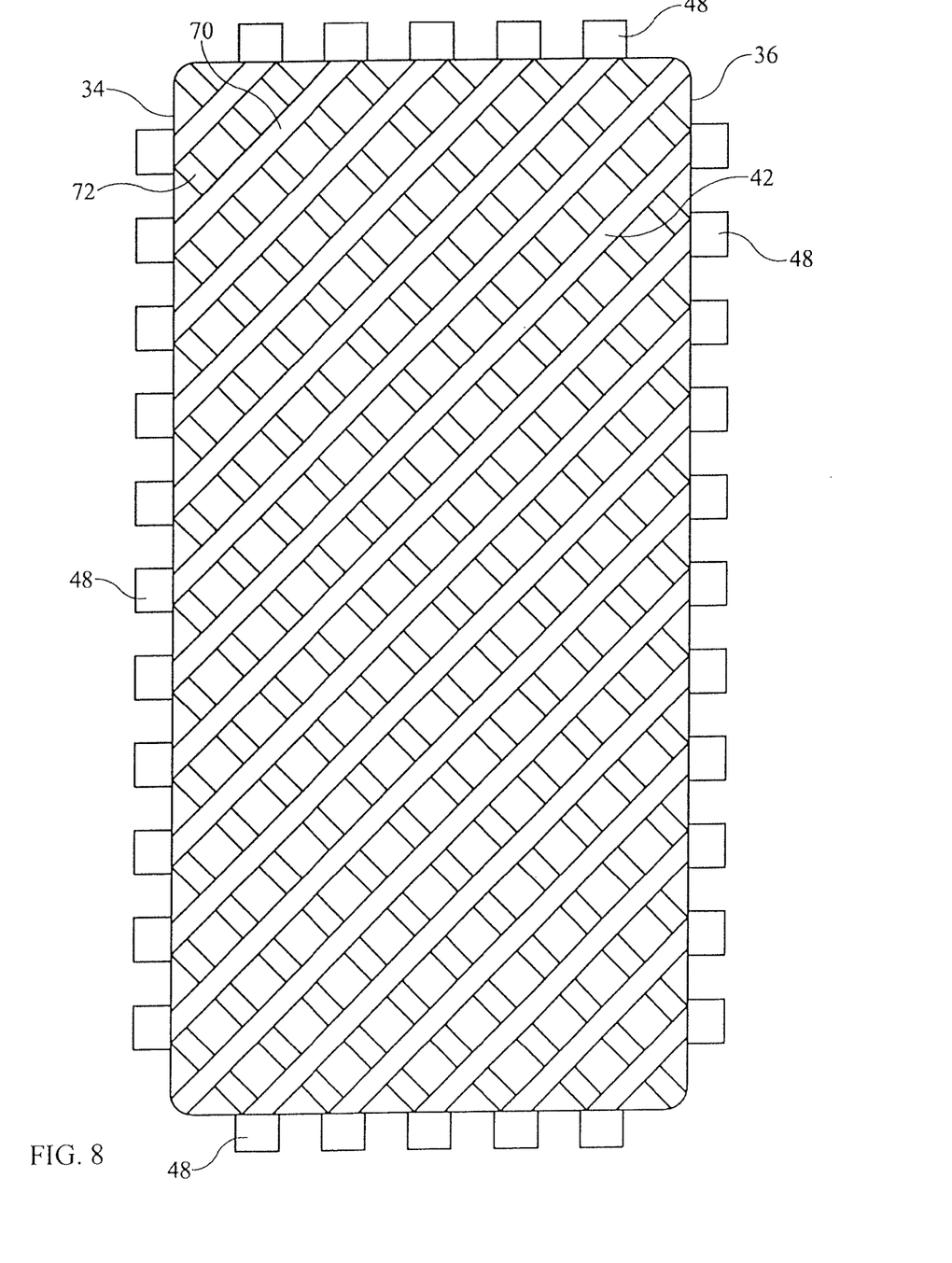
FIG. 8 is a plan view of a mattress showing a diagonal arrangement of the thermally conductive straps.

FIG. 8 shows an alternate strap configuration in which the straps, designated 70 and 72, extend diagonally rather than laterally and longitudinally.

Figure 9:
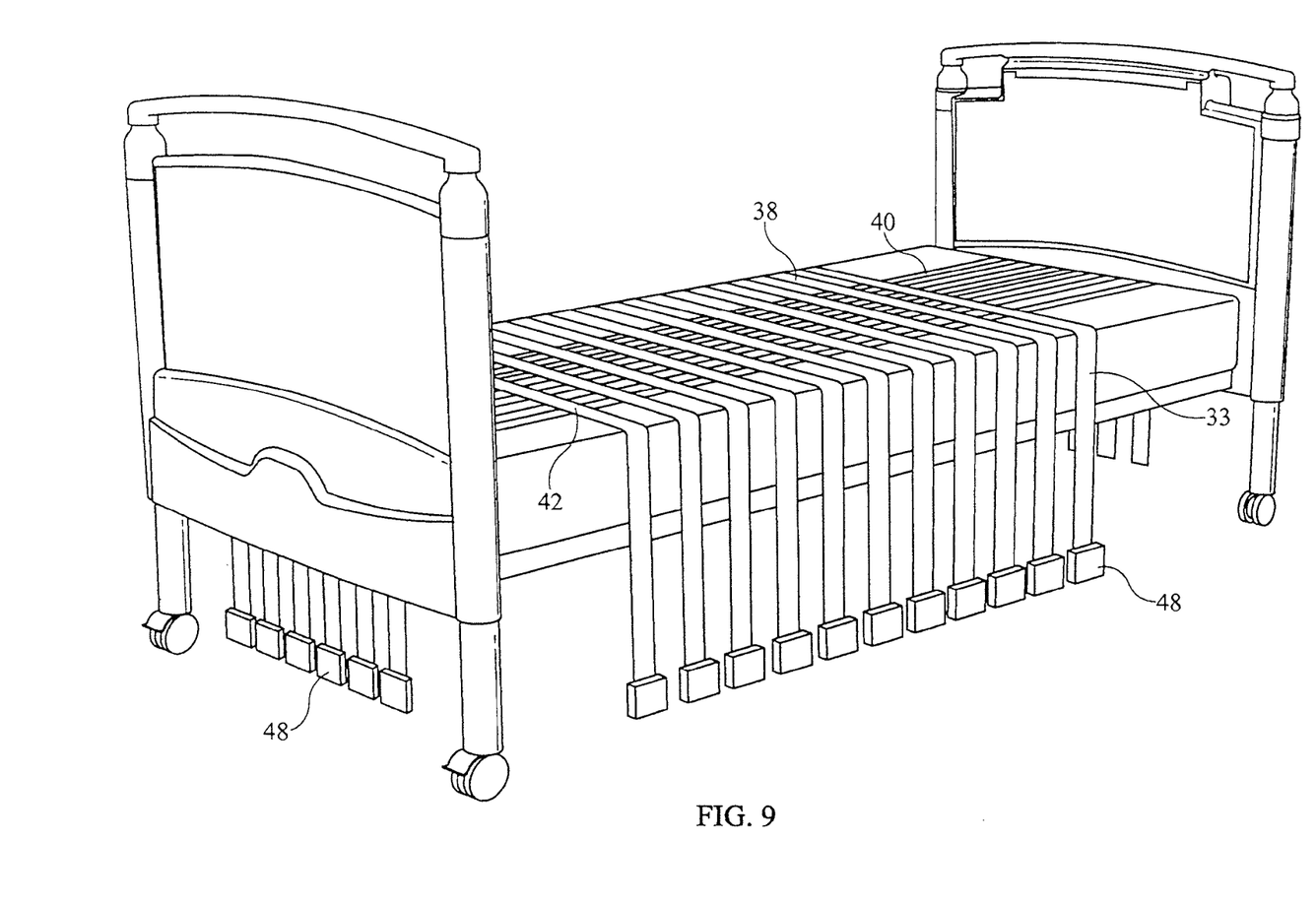
FIG. 9 is a perspective view of a bed showing an arrangement with elongated thermally conductive straps.

Another alternate configuration, shown in FIG. 9, takes advantage of the fact that the high thermal conductivity straps will extract some amount of heat from the vicinity of the bed occupant even without operation of the heat extraction modules. The configuration of FIG. 9 employs elongated straps that, unlike the straps of FIG. 1, extend vertically below the mattress. The additional strap surface area exposed to the environment increases heat withdrawal whether or not the thermoelectric modules are activated.

Figure 10:
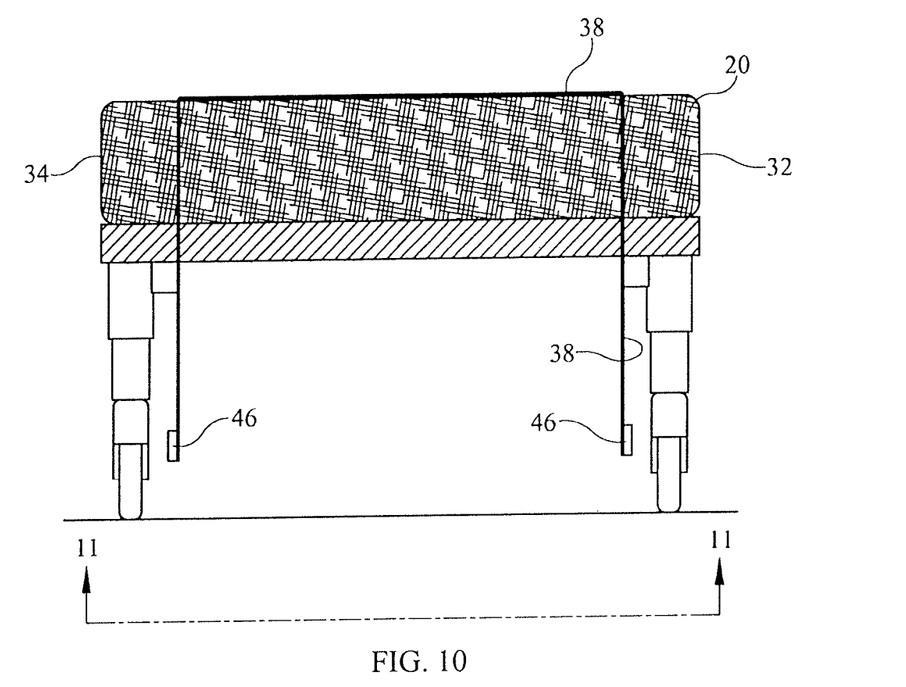
FIG. 10 is an elevation view of the bed of FIG. 9 as seen by an observer viewing the bed in the longitudinal direction.
Figure 11:
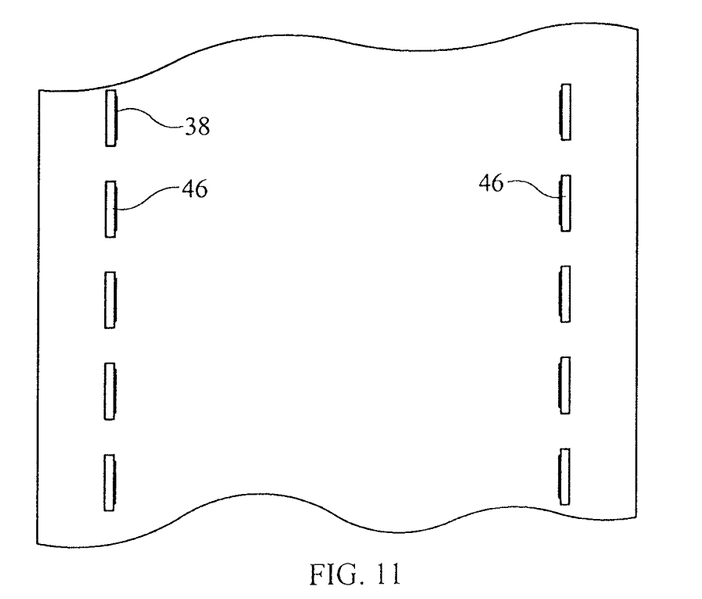
FIG. 11 is a view substantially in the direction 11-11 of FIG. 10.

FIGS. 10 and 11 show another strap arrangement in which lateral straps, rather than extending to the left and right flanks of the mattress, penetrate vertically through the mattress. Although similar to the arrangement of FIG. 9, the penetrating arrangement has the advantage that the straps are not exposed at the lateral edges of the mattress where they could be more susceptible to damage or be an annoyance to the bed occupant and visitors or staff near the mattress edge.

Figure 12:
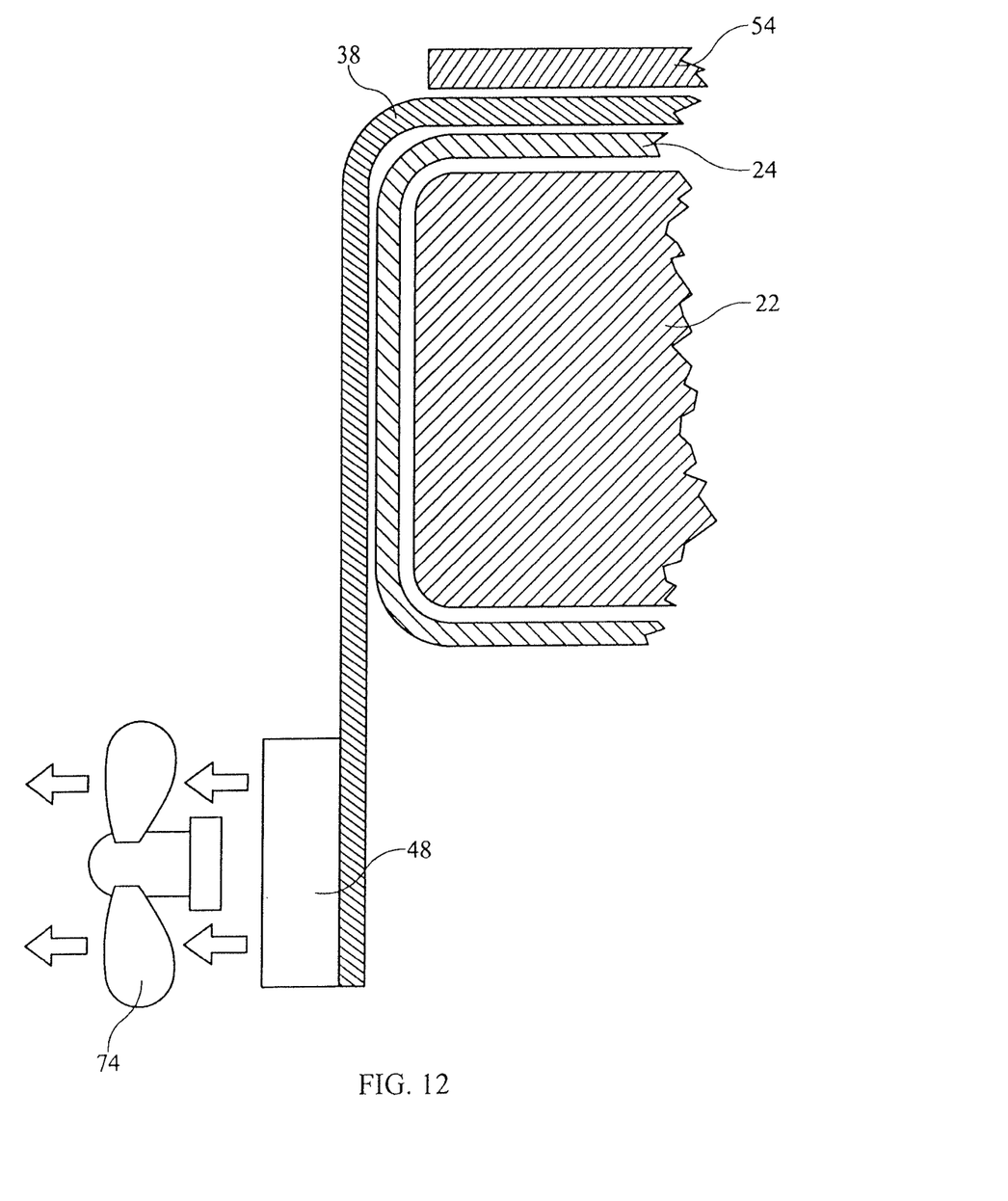
FIG. 12 is an elevation view showing an heat flow augmentor exemplified by a thermoelectric module and a fan for drawing ambient air past the module.

FIG. 12 shows an enhancement in which a fan 74 dedicated to a thermoelectric module directs ambient air over the hot side of the thermoelectric module to further enhance heat transfer.

Figure 13:
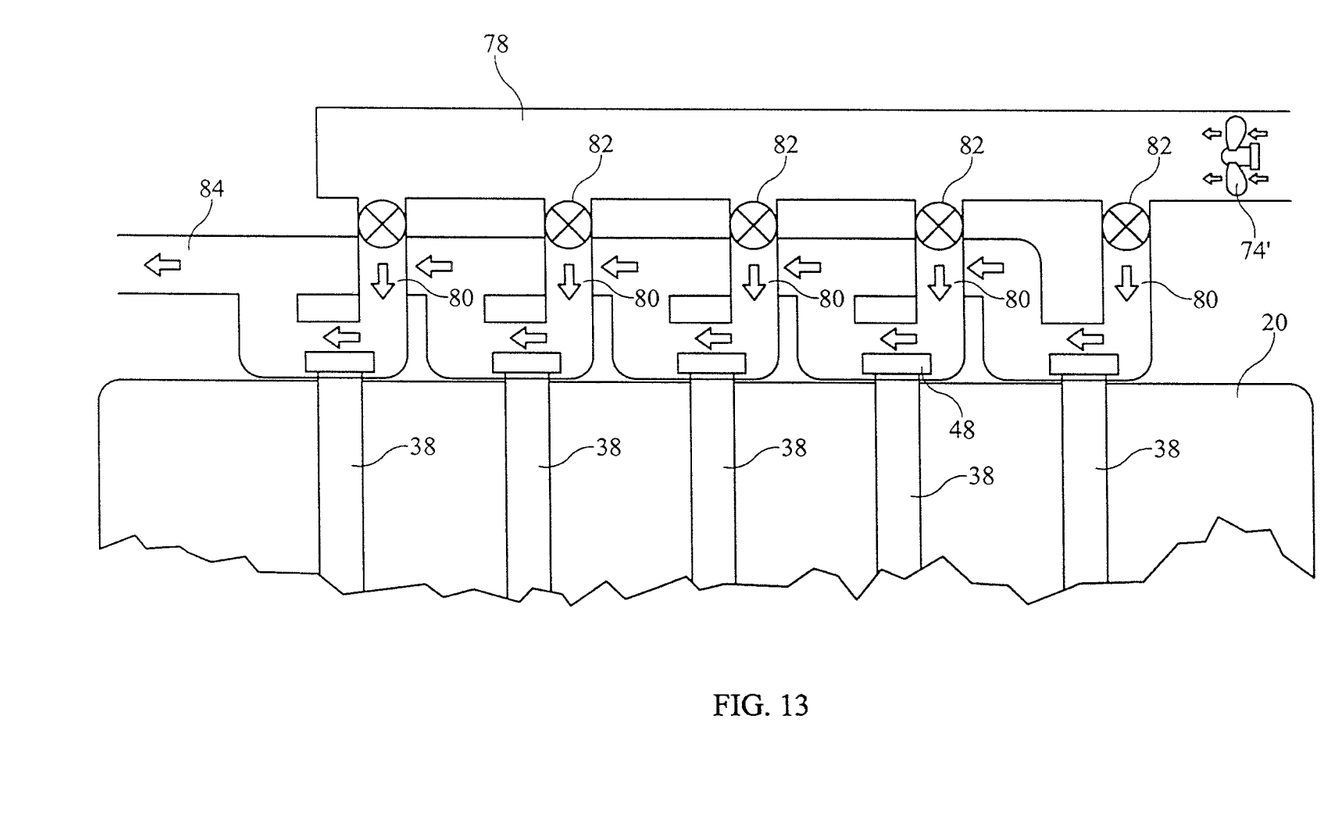
FIG. 13 is a schematic plan view of a portion of a mattress having thermally conductive lateral straps, a fan and a duct arrangement for directing ambient air through the ducts.

FIG. 13 shows an enhancement with a duct arrangement so that a single fan 74' can direct ambient air over the hot side of two or more thermoelectric module to convectively augment the heat withdrawal. The duct arrangement includes a trunk 78 and branches 80. Valves 82 under the command of controller 60 admit air at least to the branches leading to activated thermoelectric modules. A common exhaust duct 84 is provided to collect the exhaust air from all the branches.

Figure 14:
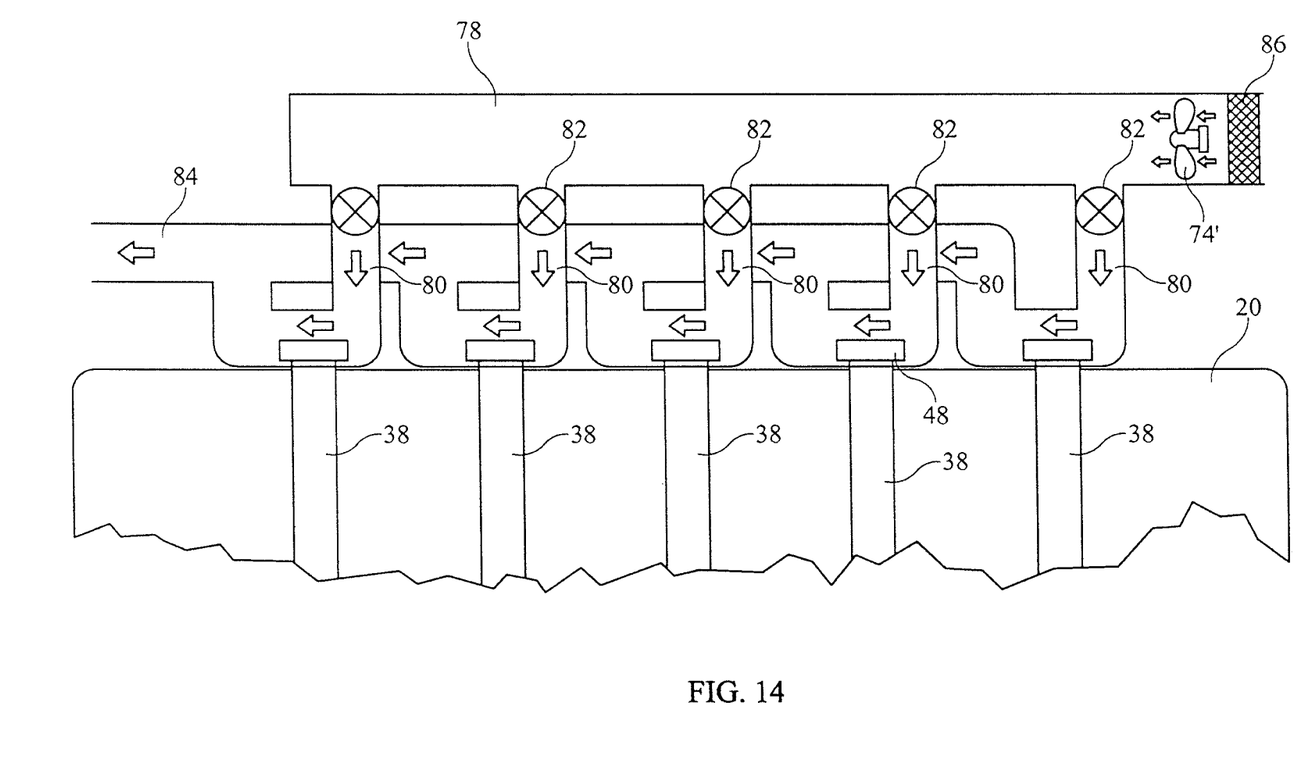
FIG. 14 is a view similar to that of FIG. 13 including a chiller for chilling the ambient air.

FIG. 14 shows an arrangement similar to that of FIG. 13 but which employs a chiller 86 to chill the air directed over the activated thermoelectric modules.

Figure 15:
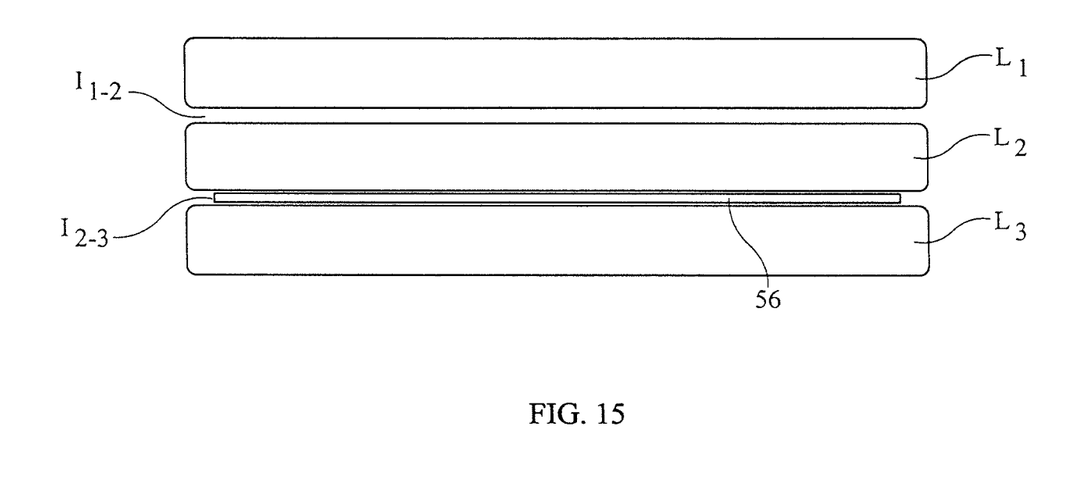
FIG. 15 is a schematic elevation view showing a multi-layer mattress.

With the certain features of the occupant support having now been described, other features and variations can now be better appreciated. The sensor array has been described as an array of pressure sensors that rests on the mattress and under a sensor cover. Accordingly, the sensor array detects interface pressure, i.e. pressure at the occupant/cover or cover/sensor interface. Alternatively, if the mattress is a multi-layer mattress, as seen in FIG. 15, the sensor array can reside between adjacent layers, e.g. layers $L_2$ and $L_3$, and sense interface pressure at the corresponding inter-layer interface $I_{2-3}$. If the mattress is one having liquid filled bladders, the sensors could be installed in the interior of the bladders so that the sensors detect intra-bladder pressure rather than an interface pressure. And although pressure sensing is thought to be a useful way to determine regions of risk, sensing other parameters, such as temperature, and/or using alternative sensing technologies might also prove satisfactory for determining regions of risk.

The mattress 20 has been shown as a bladder type mattress, however the innovations described herein can also be used with other types of mattresses such as foam mattresses. In addition, although thermoelectric modules 48 are envisioned as suitable devices for promoting localized heat withdrawal, however a wide array of other types of heat exchange devices 46 can also be used.

Although this disclosure refers to specific embodiments, it will be understood by those skilled in the art that various changes in form and detail may be made without departing from the subject matter set forth in the accompanying claims.

The invention claimed is:

1. An occupant support comprising:
   a mattress,
   a detector, and
   an energy management system comprising a plurality of straps defining thermally conductive pathways and a controller for activating a selected pathway in response to information from the detector to regulate energy transfer at a selected region of the mattress, wherein the energy management system includes a plurality of heat flow augmentors which each comprise a solid state device, each solid state device being coupled to an end region of a respective one of the plurality of straps such that opposite end regions of each of the plurality of straps have a solid state device coupled thereto, the solid state devices being configured so that, when a voltage is applied, thermal energy is transferred at the selected region.

2. The occupant support of claim 1, wherein the straps comprise thermally conductive fibers having a thermal conductivity of at least 4 watts per meter per degree Kelvin (W/m-K).

3. The occupant support of claim 1, wherein the solid state device each comprise a thermoelectric module.

4. The occupant support of claim 3, wherein the thermoelectric module has a first side and the occupant support includes a fan for causing air to flow past the first side.

5. The occupant support of claim 4, further including one fan for each thermoelectric module.

6. The occupant support of claim 3, wherein one fan causes the flow air past the first side of two or more of the thermoelectric modules.

7. The occupant support of claim 3, wherein the thermoelectric module has a first side and further comprising a chiller for producing chilled coolant and a duct system for directing the chilled coolant past the first side of one or more selected thermoelectric modules.

8. The occupant support of claim 1, wherein the detector detects pressure for use in determining the selected region.

9. The occupant support of claim 8, wherein the detected pressure comprises an interface pressure.

10. The occupant support of claim 8, further comprising one or more fluid bladders and wherein the detected pressure comprises an intra-bladder pressure.

11. The occupant support of claim 8, wherein a time rate of change of pressure is used to determine the selected region.

12. The occupant support of claim 8, wherein an interval of time during which the detected pressure exceeds a threshold pressure is used to determine the selected region.

13. The occupant support of claim 1, wherein the detector detects temperature for use in determining the selected region.

14. The occupant support of claim 1, wherein at least a portion of the plurality of straps are located inside the mattress.

15. The occupant support of claim 1, wherein the plurality of straps include a set of lateral straps and a set of longitudinal straps, the lateral and longitudinal straps defining junctures, and the selected pathway is activated by the controller issuing a command to operate a subset of the heat flow augmentors.

16. The occupant support of claim 15, wherein the controller identifies a juncture closest to the selected region and commands operation of at least one heat flow augmentor associated with the identified juncture.

17. The occupant support of claim 15, wherein the controller identifies a juncture closest to the selected region and commands operation of a heat flow augmentor closest to the identified junction and its lateral or longitudinal heat flow augmentor.

18. The occupant support of claim 15, wherein the controller identifies a juncture closest to the selected region and commands operation of all heat flow augmentors connected to the lateral and longitudinal straps that define the identified juncture.

19. The occupant support of claim 15, wherein the controller identifies a juncture closest to the selected region and commands operation of all heat flow augmentors within a specified distance of the identified juncture.

20. The occupant support of claim 15, wherein the controller identifies a juncture closest to the selected region and commands operation of a subset of the heat flow augmentors effective to cause a desired amount of thermal energy transfer.

* * * * *